United States Patent [19]
Cole et al.

[11] Patent Number: 5,429,118
[45] Date of Patent: Jul. 4, 1995

[54] DISPOSABLE MEDICAL SCOPE SHEATH

[75] Inventors: Arthur F. D. Cole, Toronto; Gerard Bruin, Mississauga; Walter R. Earle, Janetville, all of Canada

[73] Assignee: Cook (Canada) Incorporated, Canada

[21] Appl. No.: 224,044

[22] Filed: Apr. 7, 1994

[51] Int. Cl.$^6$ .................................................. A61B 1/00
[52] U.S. Cl. .................................................... 600/121
[58] Field of Search ............... 128/4, 6, 844; 138/118, 138/118.1, 121, 125, 128, DIG. 8

[56] References Cited

U.S. PATENT DOCUMENTS

| | | | |
|---|---|---|---|
| 3,809,072 | 5/1974 | Ersek et al. | 128/23 |
| 4,180,076 | 12/1979 | Betancourt | 128/349 |
| 4,195,624 | 4/1980 | Douglas | 128/8 |
| 4,271,830 | 6/1981 | Moon | 128/73 |
| 4,319,563 | 3/1982 | Kubota | 128/6 |
| 4,332,242 | 6/1982 | Chikama | 128/3 |
| 4,333,243 | 6/1982 | McLaughlin | 33/268 |
| 4,341,210 | 7/1982 | Elam | 128/207.15 |
| 4,351,342 | 9/1982 | Wiita et al. | 128/349 |
| 4,392,853 | 7/1983 | Muto | 604/171 |
| 4,470,407 | 9/1984 | Hussein | 128/6 |
| 4,497,318 | 2/1985 | Donmichael | 128/202.28 |
| 4,561,427 | 12/1985 | Takada | 128/4 |
| 4,646,722 | 3/1987 | Silverstein et al. | 128/4 |
| 4,681,093 | 7/1987 | Ono et al. | 128/6 |
| 4,721,097 | 1/1988 | D'Amelio | 128/4 |
| 4,770,188 | 9/1988 | Chikama | 128/772 |
| 4,779,611 | 10/1988 | Grooters et al. | 128/4 |
| 4,825,850 | 5/1989 | Opie et al. | 128/4 |
| 4,852,551 | 8/1989 | Opie et al. | 128/4 |
| 4,869,238 | 9/1989 | Opie et al. | 128/6 |
| 4,907,395 | 3/1990 | Opie et al. | 53/434 |
| 4,942,867 | 7/1990 | Takahashi et al. | 128/6 |
| 4,947,827 | 8/1990 | Opie et al. | 128/4 |
| 4,961,414 | 10/1990 | Cho et al. | 128/7 |
| 4,991,564 | 2/1991 | Takahashi et al. | 128/4 |
| 4,997,084 | 3/1991 | Opie et al. | 206/364 |
| 5,007,900 | 4/1991 | Picha et al. | 604/106 |
| 5,025,778 | 6/1991 | Silverstein et al. | 128/4 |
| 5,071,429 | 12/1991 | Pinchuk et al. | 606/192 |
| 5,105,800 | 4/1992 | Takahashi et al. | 128/4 |
| 5,137,032 | 8/1992 | Harmon | 128/844 |
| 5,154,164 | 10/1992 | Chikama | 128/4 |
| 5,163,950 | 11/1992 | Pinchuk et al. | 606/192 |
| 5,257,617 | 11/1993 | Takahashi | 128/4 |

*Primary Examiner*—Richard J. Apley
*Assistant Examiner*—Beverly A. Meindl
*Attorney, Agent, or Firm*—Richard J. Godlewski

[57] ABSTRACT

A disposable sheath (10) for a medical scope (11) and having a flexible, elongated body portion (13) formed from a translucent plastic material (15) with a rough-textured interior surface (19) and a flexible, transparent tip portion (22). The rough-textured interior surface includes projections (18) that result from a plurality of indentations (17) formed in the exterior surface (16) of the body portion of the sheath. The translucent plastic material of the body portion is bonded to the transparent tip portion of the sheath by high frequency heat sealing, which is pathogen impermeable. The plastic materials of the sheath are also pathogen impermeable. In one embodiment, the tip portion (46) of the sheath (33) is formed from a flat, foldable sheet (48) of plastic material. The lateral edges (51, 52) of the foldable sheet are heat sealed to each other, and the proximal edges (49, 50) are heat sealed to the distal end (47) of the body portion (35) of the sheath. The body portion is formed from two strips (36, 37) of plastic material with a shape memory for a flat configuration that are longitudinally heat sealed along the edges (38, 39) thereof. A stylet (43) is positioned in the sheath for maintaining the sheath in an open condition (42) during handling and storage.

19 Claims, 4 Drawing Sheets

DISPOSABLE MEDICAL SCOPE SHEATH

TECHNICAL FIELD

This invention relates generally to fiber optic scope sheaths and, in particular, to a disposable, medical scope sheath with a rough-textured interior surface.

BACKGROUND OF THE INVENTION

Fiber optic scopes permit visualization of the interior of various cavities in human and veterinary medicine applications. The scopes are delicate, costly devices that are typically exposed to body fluids during diagnostic or therapeutic medical procedures. When exposed to body fluids, scopes are potentially damaged by corrosive or abrasive action. Scopes also become contaminated with pathogens such as bacteria, fungi, parasites, and viruses. These pathogens can be transmitted to another patient during a subsequent procedure. The possibility of introducing an infection with an endoscope positioned in a lung, bladder, or kidney, for example, seriously impacts a generally healthy patient; however, the impact is more severe on an immuno-compromised patient such as one suffering from AIDS or following an immuno-suppression drug regimen.

The problem of contaminated scopes has previously been managed by cleaning and disinfecting a scope after each clinical use. First, the scope is mechanically cleaned with solutions to remove debris and organic matter that may be accumulated thereon or therein. The scope is then soaked in a disinfecting solution such as glutaraldehyde for at least 25 minutes, depending on the type of scope. Finally, the scope is rinsed and dried to remove all disinfectant. Special care must be taken to ensure that no traces of the toxic disinfecting solution remain on the scope, since a patient can be harmed by exposure to toxic traces. The scope also must be specially stored between clinical uses to prevent contamination after cleaning. The cleaning and disinfecting procedures are labor intensive, time consuming, and require significant handling of a scope, which can shorten the life of a scope. The chemicals used to clean and disinfect a scope can also cause deterioration to the scope, as well as cause significant health hazards to medical personnel cleaning the scope. Furthermore, some reports indicate that these cleaning and disinfecting procedures are not always effective, probably due to incomplete contaminant removal. Even when the cleaning and disinfecting procedures are successful, the best possible result is a scope that is surgically clean, not sterile.

One attempt to solve the above-mentioned problems is to use a disposable sheath that is positioned about the exterior surface of a scope for minimizing contact of the scope with body fluids. Known scope sheaths are generally formed from an elastic material tube with a closed, transparent distal end. A problem with the use of elastic material scope sheaths is that they snugly adhere to the exterior wall of the scope. As a result, the elastic material of the sheath resists deformation when the scope is bent or flexed. Therefore, the sheath is formed from a very thin piece of elastic material. Another problem with the use of thin-walled, elastic material scope sheaths is that the material is readily torn when engaging anatomical surfaces such as the teeth during a bronchoscopy or gastroscopy procedure. As a result, the scope becomes contaminated and possibly damaged due to exposure to body fluids.

Yet another problem with the use of elastic material scope sheaths is that they fit tightly around an endoscope with a high coefficient of friction. As a result, it is difficult to position a scope therein. A machine is typically used for either inflating or distending a sheath by creating a vacuum around the outside of the sheath in order to position a scope inside the sheath. The process of inflating or distending a sheath is inconvenient and costly in terms of time and equipment.

Still yet another problem with the use of elastic material scope sheaths is that the closed, transparent distal end of a sheath is typically rigid and thick. As a result, the distal end tends to behave as a lens and obstruct or distort visualization therethrough.

SUMMARY OF THE INVENTION

The foregoing problems are solved and a technical advance is achieved in an illustrative disposable, medical scope sheath having a flexible, elongated body portion of a translucent plastic material with a rough-textured interior surface for advantageously inserting a medical scope therein without tearing or stretching the plastic material and a flexible tip portion of a transparent plastic material bonded to the body portion for viewing therethrough without undue distortion. As a result, the scope sheath can be readily positioned over and removed from a medical scope without pathogen contamination of either the patient or the scope.

In one embodiment, the body portion comprises an extruded tube in which the translucent plastic material has a shape memory for a curved configuration, which readily maintains the passage extending longitudinally therethrough in an open condition for insertion and removal of the medical scope.

In another embodiment, the elongated body portion comprises a strip of translucent material having longitudinal edges bonded together. In this embodiment, the shape memory of the translucent material is set for a substantially flat configuration. However, bonding the longitudinal edges of a flat strip of translucent plastic material forms an elongated body portion and helps maintain the passage extending longitudinally therethrough in an open condition.

In a third embodiment, the elongated body portion comprises first and second strips of translucent plastic material having longitudinal edges bonded together. In this embodiment, the shape memory of the translucent plastic material is again set for a substantially flat configuration; however, at least one of the strips is shaped in another configuration other than a flat configuration for maintaining the passage of the elongated body portion in an open condition. The open passage of this embodiment is advantageously shaped with the use of a stylet which is inserted between the longitudinal strips of translucent plastic material throughout sterilization and packaging of the disposable scope sheath.

In all embodiments, the interior surface of the elongated body portion is rough textured and advantageously includes a plurality of raised projections for reducing the contact surface area between the medical scope and the sheath positioned thereover. In addition, the strips of translucent plastic material are bonded together with a heat seal that is impermeable to pathogens for advantageously maintaining the barrier quality of the plastic sheath material.

The flexible tip portion bonded to the distal end of the elongated body portion advantageously includes an end cap of a transparent plastic material, which has a smooth surface and uniform thickness to advantageously minimize distortion of the scope's viewing area.

In one aspect of the invention, the plastic material of the scope sheath comprises a polyvinyl chloride. During initial processing of polyvinyl chloride, the plastic material is translucent and has a textured surface, which does not readily adhere to the coating material of a medical scope. The textured surface is enhanced with a plurality of raised projections on the interior surface of the elongated body portion to further minimize adhesion to the medical scope. Further processing of the polyvinyl chloride causes the plastic material to become transparent with a smooth surface that readily adheres to the outer coating material of a medical scope. Advantageously, the surface area of the distal tip portion is minimized to reduce adhesion of the sheath to the medical scope. To further enhance insertion of a medical scope into the sheath, the proximal end of the elongated body portion is flared.

BRIEF DESCRIPTION OF THE DRAWINGS

FIG. 5 depicts the sheath of FIG. 4 with a stylet positioned therein for maintaining the sheath in an open condition; and FIGS. 6–9 depict the steps of making the sheath of FIGS. 4 and 5.

DETAILED DESCRIPTION

Figure 1:
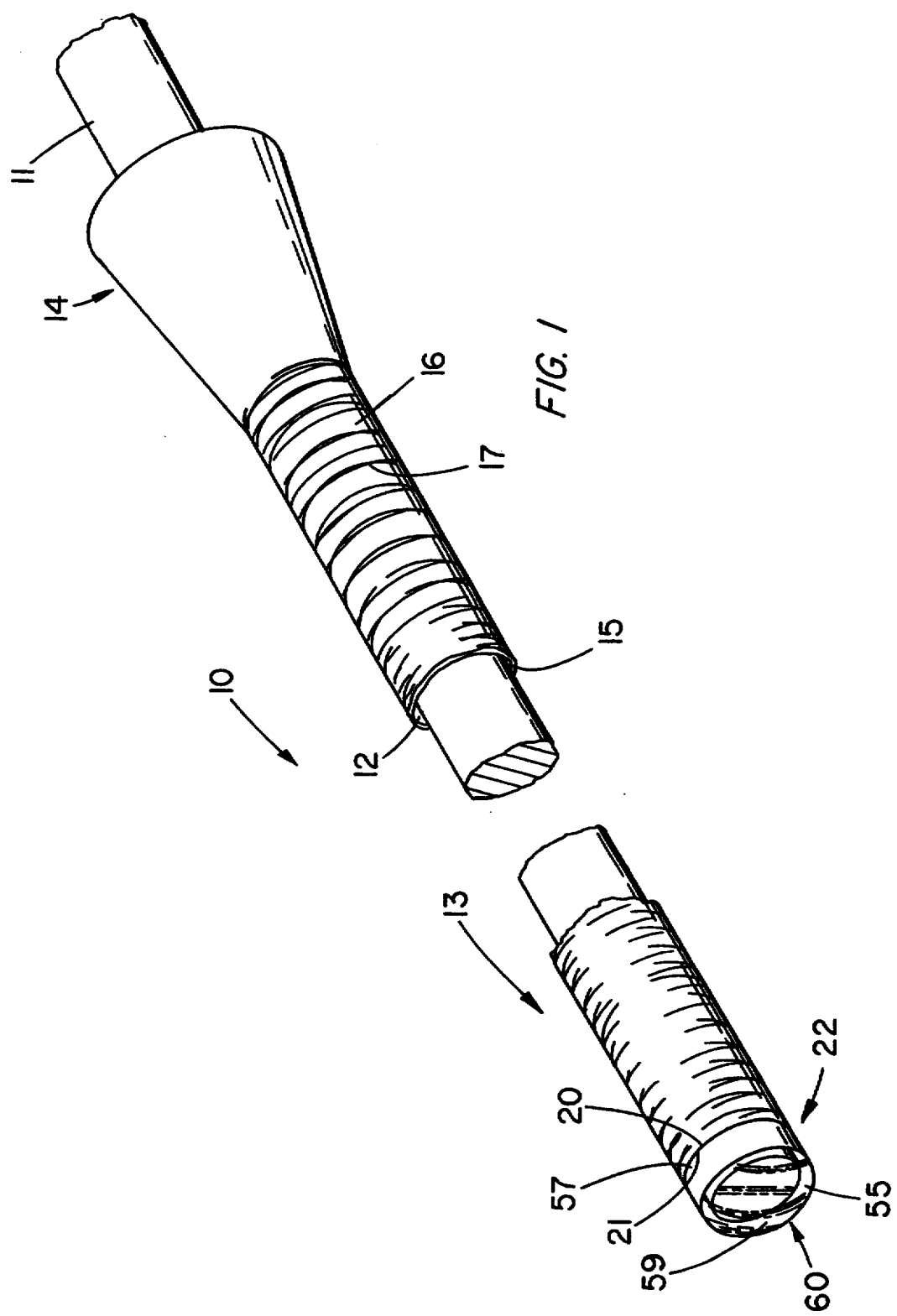
FIG. 1 depicts a longitudinal view of an illustrative disposable, medical scope sheath with a fiber optic scope positioned therein.
Figure 2:
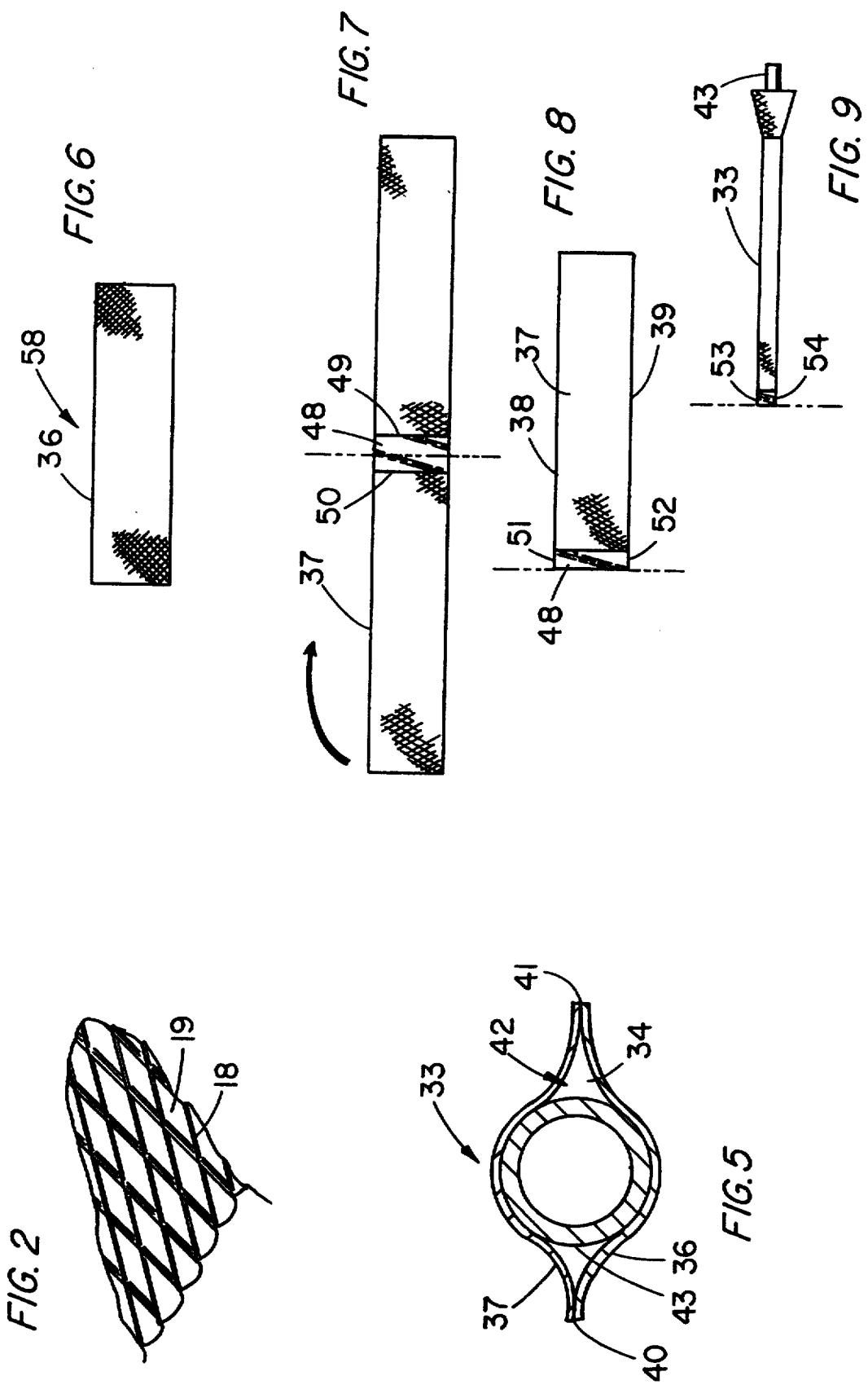
FIG. 2 depicts the rough-textured interior surface of the sheath of FIG. 1 with raised projections formed thereon.

FIG. 1 depicts a longitudinal view of an illustrative disposable, medical scope sheath 10 with fiber optic scope 11 positioned in hollow passage 12 thereof for viewing body cavities through transparent, flexible tip portion 22. Sheath 10 includes flexible, elongated body portion 13 with proximal end 14 flared for facilitating insertion of the scope into the hollow passage of the sheath. Flexible body portion 13 formed from translucent plastic material 15 has exterior surface 16 with a plurality of indentations 17 formed therein by, for example, passing the translucent plastic material between two mating dies or rollers engraved with very fine bumps which are then pressed into the material. Plurality of indentations 17 comprises, for example, a generally diamond-shaped pattern referred to as "taffeta". The indentations result in raised projections 18 that extend into hollow passage 12 of the sheath. Rough-textured interior surface 19 of the flexible body portion with raised projections 18 formed thereon, as depicted in FIG. 2, minimizes the surface area of the sheath in contact with the scope. A desirably low coefficient of friction between the sheath and scope positioned in the sheath facilitates introduction and removal of the scope.

Translucent plastic material 15 of the sheath comprises, for example, a sheet of silky frosty clear polyvinyl chloride material approximately 0.004" thick as is commercially available from Grosnor Industries, Inc., of Etobicoke, Ontario, Canada. The flexible, elongated body portion of this embodiment is formed by, for example, extruding the translucent plastic material into a length of plastic material tube with a shape memory for a tubular configuration. The translucent plastic material of the sheath is impermeable to pathogens. As a result, the sheath presents a sterile surface to the patient during clinical use despite any contamination on the surface of the scope. Polyvinyl chloride material is a desirable sheath material because it tends to resist strong acids and alkalis. Polyvinyl chloride material is also known for mechanical toughness even when formed in a thin, highly flexible layer. The silky frosty clear polyvinyl chloride material has a sheet durometer or softness of approximately 2-S.

Distal end 20 of the flexible body portion of the sheath is bonded to flexible tip portion 22 with high frequency, pathogen-impermeable heat seal 21 such as a bar seal. The flexible tip portion comprises a transparent end cap for visualization therethrough using the scope. The flexible tip portion end cap is formed from transparent plastic material 57 that is impermeable to pathogens such as, for example, a molded piece of double polished, transparent polyvinyl chloride material with smooth surface 59 and uniform thickness 60 of approximately 0.004". The smooth, uniform end cap prevents distortion of the image viewed through the scope. The transparent polyvinyl chloride material has been processed for cleaning the material and removing pigments that remain in the frosty translucent polyvinyl chloride material of the flexible body portion. A side effect of the cleaning processes required for yielding a transparent polyvinyl chloride material is that the material tends to cling or readily adhere to the surface of a scope. As a result, the transparent polyvinyl chloride material is not used to form the flexible body portion of the sheath. Flexible tip portion end cap 22 of the sheath also includes hemispherical distal surface 55 that is known to be atraumatic to patients. Although the end cap is formed to minimize harm to the patient, the end cap must also be designed to minimize distortion of the viewing field.

Figure 3:
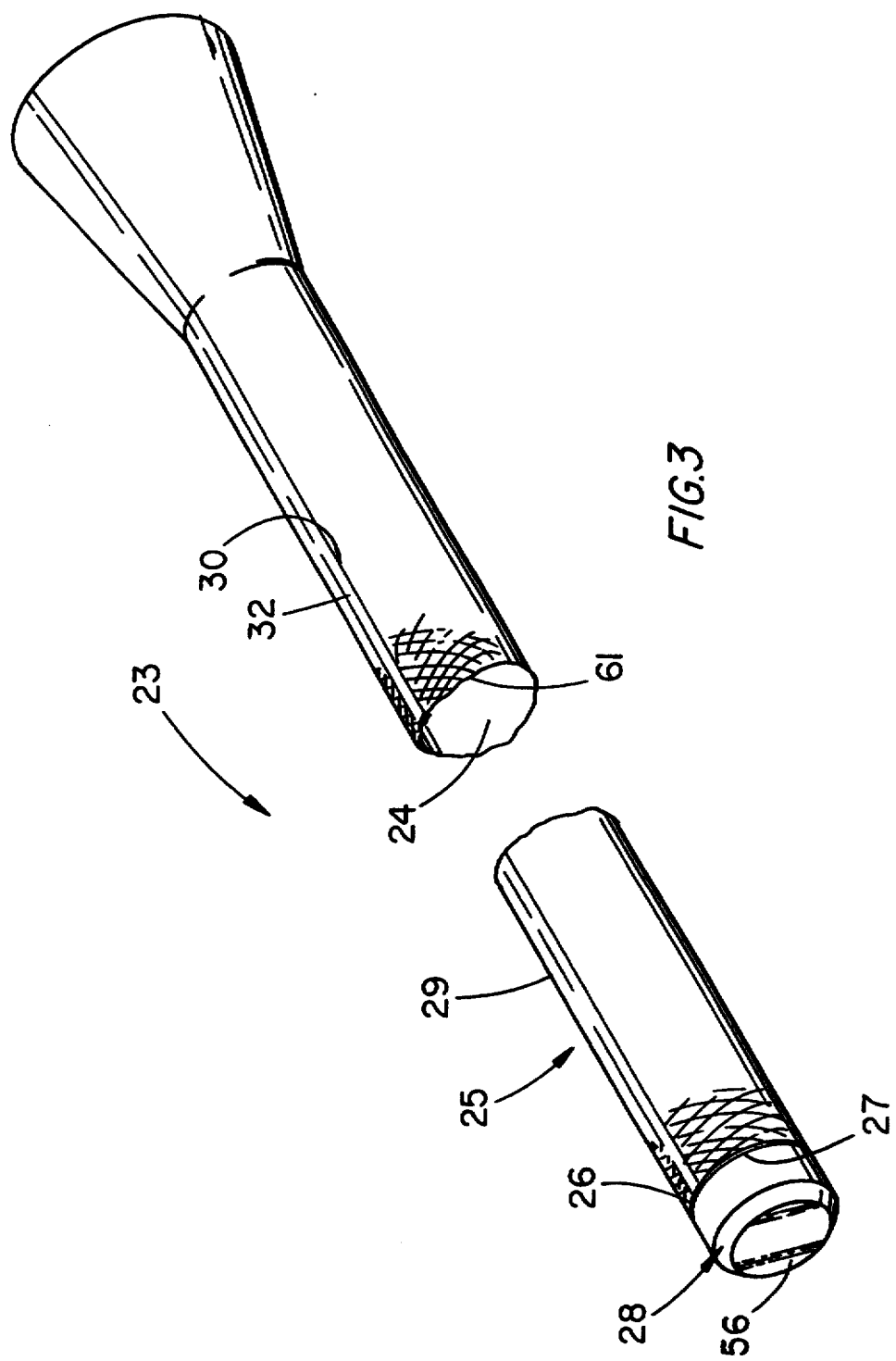
FIG. 3 depicts a longitudinal view of another disposable, medical scope sheath of the present invention.

FIG. 3 depicts a longitudinal view of another disposable, medical scope sheath 23 with rough textured interior surface 61 and hollow passage 24 extending longitudinally therethrough. Sheath 23 includes flexible, elongated body portion 25. Flexible body portion 25 of this embodiment is formed by rolling strip 29 of a flat sheet of plastic material into a tubular configuration such as over a mandril and longitudinally bonding overlapping edge 30 along pathogen-impermeable heat seal 32 such as a thin, soft, pliable seal known as a feather seal, which is approximately 1/32" wide. Strip 29 has a shape memory for a flat configuration.

Distal end 26 of the flexible body portion of the sheath is bonded at circumferential, pathogen-impermeable heat seal 27 to flexible tip portion 28, which comprises, for example, a molded end cap of transparent plastic material with a smooth surface and uniform thickness. The end cap also has flat reduced diameter distal surface 56 for reducing trauma to a patient during clinical use.

Figure 4:
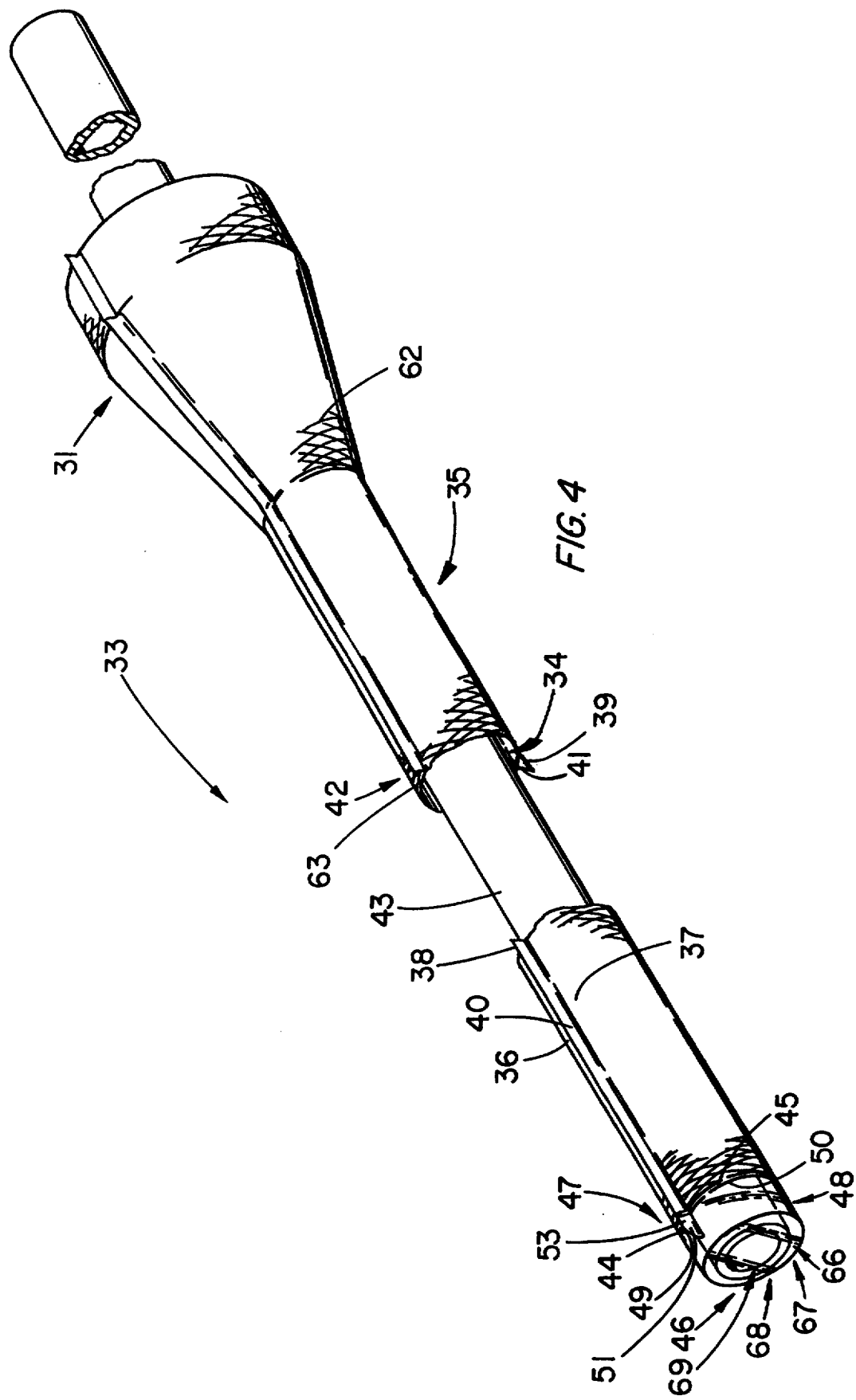
FIG. 4 depicts a longitudinal view of the best mode of the present disposable, medical scope sheath with a stylet positioned therein.

FIG. 4 depicts a longitudinal view of the best mode of the present invention in a disposable, medical scope sheath 33 with hollow passage 34 extending longitudinally therethrough and stylet 43 positioned therein. Sheath 33 includes flexible, elongated body portion 35 with flared proximal end 31. Flexible body portion 35 of this embodiment is formed from strips 36 and 37, which are longitudinally bonded at edges 38 and 39 by pathogen-impermeable heat seals 40 and 41, respectively. Strips 36 and 37 are formed from translucent plastic material 62 with rough textured interior surface 63 resulting from plurality of indentations 65 formed in exterior surface 64. The strips also have a shape memory for a flat configuration. As depicted in FIG. 5, sheath 33 with strips 36 and 37 and heat seals 40 and 41 is maintained in open condition 42 using stylet 43 positioned in hollow passage 34. Maintaining the sheath in an open condition prevents the interior surfaces of strips 36 and 37 from adhering to each other during sterilization, shipping, and storage of the sheath. The open condition eases insertion of a scope into the sheath immediately prior to clinical use. The stylet also prevents the thin, flexible strips of the sheath from creasing during handling and storage.

Strips 36 and 37 are bonded to flexible tip portion 46 about distal end 47 of the flexible body portion of the sheath. Flexible tip portion 46 comprises, for example, end cap 66 formed from folded sheet 48 of transparent plastic material 67 with smooth surface 68 and uniform thickness 69. The flexibility of the folded sheet provides a thin, malleable tip portion that readily conforms to the distal end of a fiber optic scope. As a result, the flexible tip portion prevents distortion, loss of illumination, and an undesirable "halo" effect during visualization of a body cavity. Proximal edges 49 and 50 of folded sheet 48 are bonded to strips 36 and 37 by pathogen-impermeable heat seals 44 and 45, respectively. Lateral edges 51 and 52 (not shown) of the folded sheet are also bonded together by respective, pathogen-impermeable heat seals 53 and 54 (not shown).

Stylet 43 comprises, for example, a stiff polypropylene material tube approximately 22¼" long with a ¼" outside diameter.

Flexible, elongated body portion 35 of sheath 33 is, for example, 21" long and ½" wide when measured in a generally flat configuration or closed condition. Flared proximal end 31 extends for a length of approximately 3¼" and includes a maximum width of 1¾" positioned approximately ⅜" forward from the proximal-most end of the sheath. Flexible tip portion 46 extends from the distal end of the flexible body portion for a length of 3/16" when measured in a generally flat configuration or closed condition. The width of flexible tip portion 46 approximates the width of flexible body portion 35 in this embodiment. Reduced diameter, flexible tip portion 28 of FIG. 3, for example, is 7/16" wide at heat seal 27 and narrows to ¼" wide at the distal-most end of the sheath.

Prior to clinical use, stylet 43 positioned in sheath 33 is pushed tightly against the flexible tip portion. This action is found to slightly deform the flexible tip portion end cap into the shape of the distal end of a scope. Then, the stylet is removed from the sheath and a scope positioned immediately therein. The scope is tightly applied to the flexible tip portion end cap of the sheath. As a result, the flexible tip portion readily conforms to the surface of the scope for providing visualization of a body cavity.

FIGS. 6–9 depict the steps of making sheath 33 of FIGS. 4 and 5. Strip 36, for example, is cut from a flat sheet of rough-textured, translucent plastic material, as depicted in FIG. 6. As previously mentioned, the strips of the scope sheath have a shape memory for substantially flat configuration 58. Flexible, foldable sheet 48 of transparent plastic material is bonded at proximal edges 49 and 50 to strips 36 and 37 about their distal ends by pathogen-impermeable heat sealing, as depicted in FIG. 7. To do this, two pieces of ⅛" brass rule are used to perform a 0.932" cut and form a 0.920" seal so that a 0.012" length of material extends outwardly from each seal. Foldable sheet 48 is folded precisely at its center and positioned so that strip 37 is positioned over strip 36 (not shown), as depicted in FIG. 8. Lateral edges 51 and 52 of foldable sheet 48 are bonded together at respective heat seals 53 and 54 using a feather edge brass rule and the high frequency heat sealing technique for impressing a dielectric field across the materials to be bonded together, as disclosed in U.S. Pat. No. 2,946,713 of P. Dusins, Jr. et al. Adjacent longitudinal edges 38 and 39 are also bonded by high frequency heat sealing. A flared configuration is provided about proximal end 31 of sheath 33. Proximal end 31 flares outwardly at an angle of, for example, between 20 and 40 degrees from each longitudinal seal. Excess plastic material is trimmed and removed from the exterior of the sheath. Stylet 43 is positioned in the hollow passage of sheath 33 for maintaining the sheath in an open condition, as depicted in FIG. 9.

It is to be understood that the above-described disposable, medical scope sheath is merely an illustrative embodiment of the principles of this invention and that other disposable, medical scope sheaths may be devised by those skilled in the art without departing from the spirit and scope of this invention. For example, the pathogen-impermeable bonds between the various elements of the sheath may be formed by some means other than high frequency heat sealing such as an adhesive or by a bonding process.

What is claimed is:

1. A disposable, medical scope sheath (10) comprising:

a flexible, elongated body portion (13) having a distal end (20), a proximal end (14), and a hollow passage (12) extending longitudinally therethrough and comprising a translucent plastic material (15) having a rough-textured interior surface (19) positioned around said hollow passage, said translucent plastic material having shape memory for a predetermined configuration; and a flexible tip portion (22) bonded to said distal end of said elongated body portion and comprising an end cap (55) of a transparent plastic material (57).

2. The sheath of claim 1 wherein said elongated body portion comprises a strip (29) of said translucent plastic material having longitudinal edges (30) bonded together.

3. The sheath of claim 1 wherein said elongated body portion comprises a first and a second strip (36, 37) of said translucent plastic material having longitudinal edges (38, 39) bonded together.

4. The sheath of claim 3 wherein said shape memory of said translucent plastic material is for a substantially flat configuration (58) and wherein at least one of said first and second strips is shaped in an other configuration (42) other than said flat configuration.

5. The sheath of claim 3 wherein said first and second strips are bonded together with a heat seal (40) that is impermeable to pathogens.

6. The sheath of claim 1 wherein said rough-textured interior surface (19) includes a plurality of raised projections (18).

7. The sheath of claim 6 wherein said translucent plastic material has an exterior surface (16) having a plurality of indentations (17).

8. The sheath of claim 1 wherein said transparent material has a smooth surface (59) and a uniform thickness (60).

9. The sheath of claim 8 wherein at least one of said translucent and said transparent plastic material comprises a polyvinyl chloride.

10. The sheath of claim 1 wherein said translucent material is impermeable to pathogens.

11. The sheath of claim 1 wherein said body portion has a flared proximal end (14).

12. The sheath of claim 1 further comprising a stylet (43) positioned in said hollow passage.

13. The sheath of claim 1 wherein said tip portion and said body portion are bonded together with a heat seal (21) that is impermeable to pathogens.

14. The sheath of claim 1 wherein said end cap comprises a folded sheet (48) of said transparent material having lateral edges (51, 52) bonded together and proximal edges (49, 50) bonded to said distal end of said body portion.

15. A disposable, medical scope sheath (23), comprising:
a flexible, elongated body portion (25) having a distal end (26), a proximal end, and a hollow passage (24) extending longitudinally therethrough and comprising a strip (29) of translucent plastic material having a rough-textured interior surface (61) positioned around said hollow passage, said strip of said translucent plastic material having longitudinal edges (30) bonded together, said translucent plastic material having shape memory for a substantially flat configuration (58); and
a flexible, tip portion (28) bonded to said distal end of said body portion and comprising an end cap (56) of a transparent plastic material.

16. The sheath of claim 15 further comprising a stylet (43) positioned in said hollow passage and maintaining said hollow passage in an open condition (42).

17. The sheath of claim 15 wherein said transparent material has a smooth surface (59) and a uniform thickness (60).

18. The sheath of claim 15 wherein at least one of said transparent and said translucent plastic materials comprises polyvinyl chloride and is impermeable to pathogens.

19. A disposable, medical scope sheath (33) comprising:
a flexible, elongated body portion (35) having a distal end (47), a flared proximal end (31), and a hollow passage (34) extending longitudinally therethrough and comprising a first and a second strip (36, 37) of a translucent polyvinyl chloride material (62), said translucent polyvinyl chloride material having a rough-textured interior surface (63) positioned around said hollow passage, an exterior surface (64) including a plurality of indentations (65), and shape memory for a substantially flat configuration (58), said strips of said polyvinyl chloride material having longitudinal edges (38, 39) heat sealed together;
a flexible, tip portion (46) bonded to a distal end (47) of said body portion and comprising an end cap (66) of a transparent polyvinyl chloride material (67) having a smooth surface (68) and a uniform thickness (69); and
a stylet (43) positioned in said hollow passage and maintaining said hollow passage in an open condition (42).

* * * * *